United States Patent [19]

Moyer et al.

[11] Patent Number: 5,134,141
[45] Date of Patent: Jul. 28, 1992

[54] ANTIDEPRESSANT POLYCYCLIC IMIDES TO TREAT DEPRESSION

[75] Inventors: John A. Moyer, New Hope; Gary P. Stack, Ambler, both of Pa.

[73] Assignee: American Home Products Corporation, New York, N.Y.

[21] Appl. No.: 755,721

[22] Filed: Sep. 6, 1991

[51] Int. Cl.⁵ .............................................. A61K 31/55
[52] U.S. Cl. ..................................................... 514/214
[58] Field of Search ............................................ 514/214

[56] References Cited

U.S. PATENT DOCUMENTS

| | | | |
|---|---|---|---|
| 4,797,488 | 1/1989 | Stack et al. | 544/32 |
| 4,824,999 | 4/1989 | Stack | 562/498 |
| 4,957,913 | 9/1990 | Abou-Gharbia | 514/216 |

OTHER PUBLICATIONS

Wieland, et al., Psychopharmacology, 101, 497–504 (1990).

*Primary Examiner*—S. J. Friedman
*Attorney, Agent, or Firm*—Richard K. Jackson

[57] ABSTRACT

A method for relieving depression with decahydro-3-[4-[4-(2-pyrimidinyl)-1-piperazinyl]butyl]-1,5-methano-6,7,9-metheno-2H-pentaleno[1,2-d]azepine-2,4(3H)-dione, or a pharmaceutically acceptable salt thereof.

4 Claims, No Drawings

ANTIDEPRESSANT POLYCYCLIC IMIDES TO TREAT DEPRESSION

BACKGROUND OF THE INVENTION

U.S. Pat. No. 4,797,488 discloses a series of polycyclic imides with affinity for serotonin 1A receptors useful as antipsychotic anxiolytic agents. Among these is the compound decahydro-3-[4-[4-(2-pyrimidinyl)-1-piperazinyl]butyl]-1,5-methano-6,7,9-metheno-2H-pentaleno[1,2-d]azepine-2,4(3H)-dione of the following formula (I):

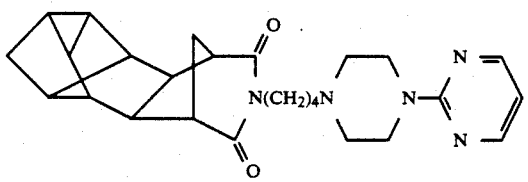

U.S. Pat. No. 4,824,999 discloses the compound 2,3,3a3b,4,5,6,6a,7,7a-decahydro-4,6,7-metheno-1H-cyclopentao[a]pentalene-1,3-dicarboxylic acid as an intermediate in the production of the corresponding anhydride from which I is prepared.

U.S. Pat. No. 4,957,913 discloses a method of treatment of rhypertension which involves administration of one of a series of serotoninergic polycyclic imides. One of these imides is decahydro-3-[4-[4-(2-pyrimidinyl)-1-piperazinyl]butyl]-1,5-methano-6,7,9-metheno-2H-pentaleno[1,2-d]azepine-2,4(3H)-dione (I).

DESCRIPTION OF THE INVENTION

In accordance with this invention there is provided a method for treating depression which comprises administering, orally or parenterally, to a patient suffering from depression, an antidepressant amount of compound I, or a pharmaceutically acceptable salt thereof.

The pharmaceutically acceptable salts are those derived from such organic and inorganic acids as: acetic, lactic, citric, tartaric, succinic, maleic, fumaric, malonic, gluconic, hydrochloric, hydrobromic, phosphoric, nitric, sulfuric, methane sulfonic, and similarly known acceptable acids.

This compound was shown to be effective in the treatment of depression in the standard forced swim behavioral despair test (Porsolt test) with rats according to the procedure outlined by Wieland and Lucki, Psychopharmacology (1990) 101:497–504. The procedure consists of a fifteen minute pretest followed by the first injection of drug. Nineteen hours later, the rat is given a second injection, followed four hours later by a third injection, and then one hour later is subjected to a five minute swim test. The test measures the amount of time the rat attempts to escape from an inescapable glass cylinder of water versus the time it spends passively floating.

The test has been used as an animal model of depression, and has had wide success in predicting antidepressant efficacy of a number of classes of drugs. Clinically effective tricyclic antidepressants such as desipramine have been shown to cause a dose dependent reduction of immobility time in the test, as have monoamine oxidase inhibitors. To test the action of compound I, groups of ten rats were administered the drug at each of a number of doses over a period of four experimental sessions. Results for the compound of this invention are shown in the following Table.

TABLE

| Saline | 8-OH-DPAT 0.5 mg/kg (s.c.) | Compound I 0.12 mg/kg | 0.25 mg/kg | 0.5 mg/kg (s.c.) |
|---|---|---|---|---|
| 196 | 126.8 | 156 | 159 | 131 |
| 154 | 108 | 126 | 142 | 162 |
| 212 | 149 | 190 | 155 | 172 |
| 228 | 148 | 79 | 148 | 110 |
| 231 | 145 | 115 | 180 | 120 |
|  |  | 148 | 150 | 107 |
|  |  | 137 | 154 | 73 |
|  |  | 138 | 150 | 94 |
|  |  | 129 | 131 | 57 |
|  | 84 | 151 | 65 |  |
| 204.2 | 135.4 | 130.2 | 152.0 | 109.1 (Mean) |
| 14.0 | 7.9 | 10.3 | 4.0 | 12.2 (sem) |

Table 1:
Data for Compound 1. The numbers represent secondsspent immobile out of a possible 300.

Thus, the compound of this invention was found to decrease immobility time by as much as fifty percent compared to saline. By comparison, a 10 mg/kg dose of the antidepressant desmethylimipramine decreased immobility by twenty-eight percent compared to saline. These results indicate that the compound of the invention is a potent antidepressant, useful for the treatment of depression and other disorders commonly treated by the administration of antidepressants agents, such as obsessive-compulsive disorder (OCD), panic disorder, eating disorders such as bulimia or anorexia nervosa, sexual dysfunction, addiction to alcohol or cocaine, dementia due to stroke or neurodegenerative disease and migraine.

As such, this may be administered neat or with a pharmaceutical carrier to a patient in need thereof. The pharmaceutical carrier may be solid or liquid. A solid carrier can include one or more substances which may also act as flavoring agents, lubricants, solubilizers, suspending agents, fillers, glidants, compression aids, binders or tablet-disintegrating agents. It can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example calcium phosphate, magnesium stearate, talc, sugars, lactose, dextrin, starch, gelatin cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. In addition, the antidepressant agent of this invention may be administered subdermally in solid depot form for relatively long term (6 months to 5 years) treatment of chronic depression.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific depression must be subjectively determined by the attending physician. The variables involved include the level of depression and the size, age and response pattern of the patient. Based on the activity profile and potency of the compound tested, supra, an initial human dose within the range of about 10 to about 50 mg/day, by single or divided, oral administration, should be appropriate. The continuing dose may then be modified to achieve the desired effect, within the range of 5 to 200 mg/day or more, as personalized for the patient.

The compound of the invention is disclosed in U.S. Pat. Nos. 4,797,488; 4,824,999; and 4,957,913. Its preparation is illustrated in the following Example.

EXAMPLE

Decahydro-3-[4-[4-(2-pyrimidinyl)-1-piperazinyl]-butyl]-1,5-methano-6,7,9-metheno-2H-pentaleno[1,2-d]azepine-2,4(3H)-dione Potassium permanganate (50 g, 0.32 mmoles) was dissolved in 500 ml of water in a 1 l three neck flask equipped with a thermometer, addition funnel and overhead stirrer. To it was added a solution of 18.4 g (0.10 mole) of norbornadiene dimer and 5.0 g (18 mmoles) of tetra-n-butylammonium chloride in 300 ml of benzene.

The reaction temperature was kept below 40 degrees C by means of a cold water bath. The solution was stirred overnight at room temperature; then 60 g of sodium bisulfite was added and the mixture was acidified with concentrated hydrochloric acid. Five hundred milliliters of ethyl acetate was added and the organic phase was removed in a separatory funnel. The aqueous phase was extracted with two additional 500 ml portions of ethyl acetate. The combined organic portions were washed with 300 ml. saturated brine, dried over $Na_2SO_4$, filtered, and evaporated to obtain 24 g of 2,3,3a,3b,4,5,6,6a,7,7a-decahydro-4,6,7-metheno-1H-cyclopenta[a]pentalene-1,3-dicarboxylic acid.

The diacid prepared above (2.5 g, 10 mmoles) was combined with 2.4 g (10 mmoles) of 1-(4-aminobutyl)-4-(2-pyrimidinyl)piperazine in 300 ml of xylene and refluxed under nitrogen for 48 hours with water separation via a Dean-Stark trap. The mixture was allowed to cool, concentrated in vacuum and filtered through 75 g of silica gel in 2% $EtOH/CHCl_3$. Concentration in vacuum and recrystallization from isopropanol with the addition of 4N HCl/isopropanol gave a pale pink solid title compound as the dihydrochloride, hemihydrate, 820 mg, m.p. 229–231 degrees C.

Elemental analysis for $C_{26}H_{33}N_5O_2 \cdot 2HCl \cdot \frac{1}{2}H_2O$: Calc'd: C, 58.98; H, 6,85; N, 13.23; Found: C, 59.26; H, 6.78; N, 13.04.

What is claimed is:

1. A process for relieving depression in a depressed patient which comprises administering, orally or parenterally, an antidepressant amount of decahydro-3-[4-[4-(2-pyrimidinyl)-1-piperazinyl]butyl]-1,5-methano-6,7,9-metheno-2H-pentaleno[1,2-d]azepine-2,4(3H-dione, or a pharmaceutically acceptable salt thereof.

2. A process of claim 1 in which decahydro-3-[4-[4-(2-pyrimidinyl)-1-piperazinyl]butyl]-1,5-methano-6,7,9-metheno-2H-pentaleno[1,2-d]azepine-2,4(3H-dione, or a pharmaceutically acceptable salt thereof is administered orally.

3. A process of claim 1 in which decahydro-3-[4-[4-(2-pyrimidinyl)-1-piperazinyl]butyl]-1,5-methano-6,7,9-metheno-2H-pentaleno[1,2-d]azepine-2,4(3H-dione, or a pharmaceutically acceptable salt thereof is administered parenterally.

4. A process of claim 1 in which decahydro-3-[4-[4-(2-pyrimidinyl)-1-piperazinyl]butyl]-1,5-methano-6,7,9-metheno-2H-pentaleno[1,2-d]azepine-2,4(3H-dione, or a pharmaceutically acceptable salt thereof is administered subdermally in solid depot form.

* * * * *